(12) United States Patent
Kelley et al.

(10) Patent No.: US 11,543,399 B2
(45) Date of Patent: Jan. 3, 2023

(54) REAGENTS FOR ENHANCED DETECTION OF LOW VOLATILITY ANALYTES

(71) Applicant: Massachusetts Institute of Technology, Cambridge, MA (US)

(72) Inventors: Jude A. Kelley, Sutton, MA (US); Roderick Russell Kunz, Acton, MA (US); Alla Ostrinskaya, Needham, MA (US); Richard Paul Kingsborough, Groton, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 435 days.

(21) Appl. No.: 16/506,780

(22) Filed: Jul. 9, 2019

(65) Prior Publication Data

US 2020/0011844 A1    Jan. 9, 2020

Related U.S. Application Data

(60) Continuation-in-part of application No. 15/435,733, filed on Feb. 17, 2017, now Pat. No. 11,237,143, and
(Continued)

(51) Int. Cl.
*G01N 33/22*  (2006.01)
*G01N 27/623*  (2021.01)

(52) U.S. Cl.
CPC ......... *G01N 33/227* (2013.01); *G01N 27/623* (2021.01); *Y10T 436/19* (2015.01); *Y10T 436/24* (2015.01)

(58) Field of Classification Search
None
See application file for complete search history.

(56) References Cited

U.S. PATENT DOCUMENTS 4,201,839 A    5/1980   Johnson
4,242,097 A    12/1980  Rich, Jr. et al.
(Continued)

FOREIGN PATENT DOCUMENTS

EP    1145005 A2   10/2001
EP    1844189 A2   10/2007
(Continued)

OTHER PUBLICATIONS

International Preliminary Report on Patentability for PCT/US2013/051676, dated Jan. 27, 2015: 8 pages.
(Continued)

*Primary Examiner* — Paul S Hyun

(57) ABSTRACT

The use of volatilization reagents is disclosed for improved detection of inorganic oxidizers such as, but not limited to, chlorates and perchlorates. Detection methods are disclosed whereby a reagent can transfer a proton to the anion (i.e., chlorate, perchlorate, etc.) of an inorganic salt analyte, forming an acid (i.e., chloric acid, perchloric acid) that is easier to detect by a mechanism whereby the acidified reagent is more easily vaporized, and hence, more easily detected. Concurrently, the anion of the acid forms a new salt with the cation released from the salt that was acidified. The reagents can also include acidic salts or cation-donators, more generally. In some embodiments, hydrated reagents or co-reagents that can release water can be employed.

11 Claims, 16 Drawing Sheets

Related U.S. Application Data a continuation-in-part of application No. 14/679,891, filed on Apr. 6, 2015, now Pat. No. 10,345,281, said application No. 15/435,733 is a division of application No. 13/948,423, filed on Jul. 23, 2013, now Pat. No. 9,588,095, and a continuation-in-part of application No. 13/832,905, filed on Mar. 15, 2013, now Pat. No. 9,891,193.

(60) Provisional application No. 61/975,275, filed on Apr. 4, 2014, provisional application No. 61/806,636, filed on Mar. 29, 2013, provisional application No. 61/674,980, filed on Jul. 24, 2012.

(56) References Cited

U.S. PATENT DOCUMENTS

| | | | |
|---|---|---|---|
| 4,387,164 | A | 6/1983 | Hevey et al. |
| 4,562,148 | A | 12/1985 | Sommer |
| 4,752,448 | A | 6/1988 | Wells et al. |
| 5,157,260 | A | 10/1992 | Mylchreest et al. |
| 5,296,380 | A | 3/1994 | Margalit |
| 5,352,893 | A | 10/1994 | Freedman |
| 5,756,994 | A | 5/1998 | Bajic |
| 5,988,002 | A | 11/1999 | Danylewych-May et al. |
| 6,287,780 | B1 | 9/2001 | Schmidt et al. |
| 6,627,444 | B1 | 9/2003 | Goledzinowski et al. |
| 7,078,237 | B1 | 7/2006 | Mowry et al. |
| 7,439,496 | B1 | 10/2008 | Stott et al. |
| 7,534,844 | B2 | 5/2009 | Kwak |
| 7,598,488 | B2 | 10/2009 | Park |
| 7,638,266 | B2 | 12/2009 | Angelopoulus et al. |
| 8,119,984 | B2 | 2/2012 | Shabanowitz et al. |
| 8,217,340 | B2 | 7/2012 | Yoshimura et al. |
| 8,304,251 | B2 | 11/2012 | Haas et al. |
| 8,513,596 | B2 | 8/2013 | Kang et al. |
| 9,588,095 | B2 | 3/2017 | Gregory et al. |
| 9,891,193 | B2 | 2/2018 | Gregory et al. |
| 10,345,281 | B2 | 7/2019 | Kelley et al. |
| 2004/0157344 | A1 | 8/2004 | Wang et al. |
| 2005/0288616 | A1 | 12/2005 | Bozenbury et al. |
| 2006/0192098 | A1 | 8/2006 | Danylewych-May |
| 2007/0069120 | A1 | 3/2007 | Shvartsburg |
| 2008/0101995 | A1 | 5/2008 | Gabowitcz et al. |
| 2008/0128608 | A1 | 6/2008 | Northen et al. |
| 2008/0245963 | A1 | 10/2008 | Land et al. |
| 2009/0032701 | A1 | 2/2009 | Rodier et al. |
| 2009/0039243 | A1 | 2/2009 | Wynn et al. |
| 2009/0078862 | A1 | 3/2009 | Rodier et al. |
| 2009/0269855 | A1 | 10/2009 | Wang et al. |
| 2010/0047849 | A1 | 2/2010 | Caulfield et al. |
| 2010/0291704 | A1 | 11/2010 | Cody |
| 2011/0020941 | A1* | 1/2011 | Rudd ............... G01N 33/5308 436/63 |
| 2011/0081723 | A1 | 4/2011 | Miller et al. |
| 2011/0101216 | A1 | 5/2011 | Musselman |
| 2012/0119079 | A1 | 5/2012 | Ouang et al. |
| 2012/0149006 | A1 | 6/2012 | Padilla De Jesus et al. |
| 2012/0181421 | A1 | 7/2012 | Satoh |
| 2014/0030816 | A1 | 1/2014 | Gregory et al. |
| 2014/0065550 | A1 | 3/2014 | Kramer et al. |

FOREIGN PATENT DOCUMENTS

| | | |
|---|---|---|
| WO | 1999005319 A2 | 2/1999 |
| WO | 2000075372 A1 | 12/2000 |
| WO | 2007066240 A2 | 6/2007 |
| WO | 2009152276 A2 | 12/2009 |
| WO | 2011144743 A1 | 11/2011 |

OTHER PUBLICATIONS

International Search Report and Written Opinion for PCT/US2013/051671, dated Apr. 4, 2014: 10 pages.

Sakayanagi et al., "Identification of inorganic anions by gas chromatography/mass spectrometry" Forensic Science International 157 (2006) 134-143.

Oscar Yanes, Hin-Koon Woo, Trent R. Northen, Stacey R. Oppenheimer, Leah Shriver, Jon Apon, Mayra N. Estrada, Michael J. Potchoiba, Rick Steenwyk, Marianne Manchester, and Gary Siuzdak "Nanostructure Initiator Mass Spectrometry: Tissue Imaging andDirect Biofluid Analysis" Anal. Chem. 2009, 81, 2969-2975.

Hadis Morkoc "Handbook of Nitride Semiconductors and Devices, Materials Properties, Physics and Growth" Jul. 30, 2009.

Sundberg, R. J.; Carey, F. A., Advanced Organic Chemistry, Part B: Reactions and Synthesis, 5th Edition, Springer, 2007. Table of contents.

Brodbelt, J. S.; Liou, C. C., New frontiers in host-guest chemistry—the gas phase. Pure and Applied Chemistry 1993, 65 (3), pp. 409-414.

Chu, I. H. et al., Macrocyclic chemistry in the gas phase—intrinsic cation affinities and complexation rates for alkali-metal cation complexes of crown-ethers and glymes. Journal of the American Chemical Society 1993, 115 (13), pp. 5736-5744.

De Perre, C. et al., Rapid and specific detection of urea nitrate and ammonium nitrate by electrospray ionization time-of-flight mass spectrometry using infusion with crown ethers. Rapid Communications in Mass Spectrometry 2012, 26 (2), pp. 154-162.

Dietrich, B.; Kintzinger et al., Stability, molecular-dynamics in solution, and x-ray structure of the ammonium cryptate $NH_4^+$ subset of 2.2.2.$PF_6$. Journal of Physical Chemistry 1987, 91 (27), pp. 6600-6606.

Eiceman, G. A. et al., Enhanced selectivity in ion mobility spectrometry analysis of complex mixtures by alternate reagent gas chemistry. Analytics Chimica Acta 1995, 306 (1), pp. 21-33.

Evans, C. S. et al., A rapid and efficient mass spectrometric method for the analysis of explosives. Rapid Communications in Mass Spectrometry 2002, 16 (19), pp. 1883-1891.

Ewing, R. G. et al., A critical review of ion mobility spectrometry for the detection of explosives and explosive related compounds. Taianta 2001, 54 (3), pp. 515-529.

Flanigan, P. M. et al., Determination of Inorganic Improvised Explosive Device Signatures Using Laser Electrospray Mass Spectrometry Detection with Offline Classification. Analytical Chemistry 2011, 83 (18), pp. 7115-7122.

Graf, E. et al.. Molecular recognition—selective ammonium cryptates of synthetic receptor molecules possessing a tetrahedral recognition site. Journal of the American Chemical Society 1982, 104 (6), pp. 1672-1678.

Kozole, J.; et al., Characterizing the gas phase ion chemistry of an ion trap mobility spectrometry based explosive trace detector using a tandem mass spectrometer. Taianta 2012, 99, pp. 799-810.

Lawrence, A. H.; Neudorf, P., Detection of ethylene glycol dinitrate vapors by ion mobility spectrometry using chloride reagent ions. Analytical Chemistry 1988, 60 (2), pp. 104-109.

Maleknia, S.; Brodbelt, J., Cavity-size-dependent dissociation of crown-ether ammonium ion complexes in the gas-phase. Journal of the American Chemical Society 1993, 115 (7), pp. 2837-2843.

More, M. B.; et al. Intrinsic affinities of alkali cations for 15-crown-5 and 18-crown-6: Bond dissociation energies of gas-phase M+-crown ether complexes. Journal of the American Chemical Society 1999, 121 (2), pp. 417-423.

Park, K.-M. et al., Surprisingly stable ammonium ion complex of a non-cyclic crown-type polyether: Solid and solution studies. New Journal of Chemistry 2010, 34 (4), pp. 603-606.

Sassine, A. et al. .; Felinto, M. C. F. C., An electrospray ionization tandem mass spectrometric study of p-tert-butylcalix[6]arene complexation with ammonium hydroxide, and ammonium and sodium ions. Rapid Communications in Mass Spectrometry 2008, 22 (3), pp. 385-393.

Spath, A. et al., Molecular recognition of organic ammonium ions in solution using synthetic receptors. Beilstein Journal of Organic Chemistry 2010, 6.

Taylor, V. F. et al., A mass spectrometric study of glucose, sucrose, and fructose using an inductively coupled plasma and electrospray ionization. International Journal of Mass Spectrometry 2005, 243 (1), pp. 71-84.

(56) References Cited

OTHER PUBLICATIONS

Tsai, C.W. et al. Analysis of ammonium nitrate/urea nitrate with crown ether and sugar as modifiers, American Society for Mass Spectrometry, Denver, 2011.

Badu-Tawiah, A. K. et al. Reactions of microsolvated organic compounds at ambient surfaces: Droplet velocity, charge state, and solvent effects. Journal of the American Society for Mass Spectrometry 2012, 23 (6), pp. 1077-1084.

Benassi, M. et al. Redox transformations in desorption electrospray ionization, International Journal of Mass Spectrometry 2009, 280, pp. 325-240.

Fieser, M., Fiesers' Reagents for Organic Synthesis, vol. 27, John Wley & Sons, 2011. Table of contents.

McDougall, J.L.; Simkins, R.J.J., The identification of traces of explosives by field spot tests in Ministry of Defense Explosives Research and Development Establishment, Technical Report No. 122, Mar. 1973.

Smith, M., March's Advanced Organic Chemistry: Reactions, Mechanisms and Structure, 7th Edition, Wiley & Sons, 2013. Table of contents.

Urbansky, E.T.; et al. Quantitation of perchlorate ion by electrospray ionization mass spectrometry (ESI-MS) using stable association complexes with organic cations and bases to enhance selectivity, Journal of Analytical Atomic Spectrometry 1999, 14, pp. 1861-1866.

Yongtao, Li et al., Reversed-phase liquid chromatography/ electrospray ionization/mass sppectometry with isotope dilution for the analysis of nitrate and nitrite in water; Journal of Chromatograph A, 1218 2011 pp. 476-483.

Masataka Sakayanagi et al., Identification of inorganic anions by gas chromatography/mass spectrometry, Forensic Science International 157 2006 pp. 134-143.

International Search Report and the Written Opinion for PCT/US2013/051676, dated May 27, 2014 (11 pages.).

International Preliminary Report on Patentability (IPRP) and Written Opinion for PCT/US2013/051676, dated Jan. 27, 2015 (8 pages).

"18-Crown-6" accessed by examiner at [http://www.chemicalland21.com/lifescience/phar/18-crown-6.htm] on Apr. 1, 2014.

3-Pyridinecarboxamide (nicotinamide) (UNEP Publications Oct. 2002) accessed by examiner at [http://www.inchem.org/documents/sids/sids/98920.pdf].

IARC Monographs vol. 73 "Hexachloroethane" was accessed by the examiner from [http://monographs.iarcs.fr/ENG/Monographs/vol73/mono73-15.pdf] on Dec. 22, 2014.

International Search Report and Written Opinion received in PCT/US2015/24560 dated Jun. 29, 2015; 13 pages.

Li et al., Reversed-phase liquid chromatography/electrospray ionization/ mass spectrometry with isotope dilution for the analysis of nitrate and nitrite in water. Journal of Chromatography A. Jan. 21, 2011; 1218 (3): 476-483.

Morkoc., "Handbook of Nitride Semiconductors and Devices, Materials Properties, Physics and Growth" Jul. 30, 2009.

Office Action received in related U.S. Appl. No. 13/948,423 dated Aug. 10, 2016; 18 pages.

Schmitt-Kopplin P et al., "Capillary electrophoresis—electrosprayionization—mass spectrometry for the characterization of natural organic matter:an evaluation with free flow electrophoresis-off-line flow injection electrosprayionization-mass spectrometry." Electrophoresis. Sep. 2003;24(17):3057-66.

Yanes et al., "Nanostructure Initiator Mass Spectrometry: Tissue Imaging and Direct Biofluid Analysis" Anal. Chem. 2009, 81, 2969-2975.

Office Action dated Jan. 31, 2018, in related U.S. Appl. No. 14/679,891, pages (17).

PCT International Preliminary Report on Patentability and PCT Written Opinion of the International Searching Authority for PCT/US2013/051676, dated Jan. 27, 2015 (8 pages.).

PCT Notification of Transmittal of the International Search Report and the Written Opinion of the International Searching Authority, or the Declaration, PCT/US2013/051676, dated May 27, 2014 (11 pages.).

U.S. Appl. No. 13/832,905, filed Mar. 15, 2013, Reagent Impregnated Swipe for Chemical Detection.

PCT/US13/51671, Jul. 23, 2013, Reagent Impregnated Swipe for Chemical Detection.

PCT/US13/51676, Jul. 23, 2013, Reagents for Oxidizer-Based Chemical Detection.

Schenderlein et al.,Preparation and characterization of light-switchable polymer networks attached to solid substrates. Langmuir. Apr. 9, 2013;29(14):4525-34.

\* cited by examiner

Representative Reactions a.) $HCl + KClO_3 \rightarrow HClO_3 + KCl$ b.) $HCl + KClO_4 \rightarrow HClO_4 + KCl$ c.) $H_2SO_4 + 2\,KClO_3 \rightarrow 2\,HClO_3 + K_2SO_4$ d.) $H_2SO_4 + 2\,KClO_4 \rightarrow 2\,HClO_4 + K_2SO_4$ e.) $NaHSO_4 + KClO_3 \rightarrow HClO_3 + NaKSO_4$ f.) $NaHSO_4 + KClO_4 \rightarrow HClO_4 + NaKSO_4$ g.) $Na_2S_2O_3 \cdot 5H_2O \xrightarrow{\Delta q} Na_2S_2O_3 + 5H_2O$

*FIG. 3*

Nafion

Polystyrene Sulfonic Acid

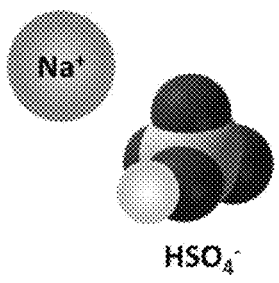
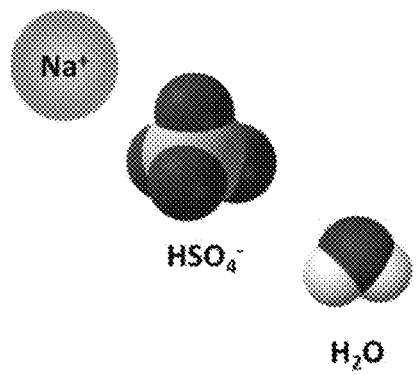
Anhydrous Sodium Bisulfate (solid)　　Sodium Bisulfate Monohydrate (solid)
*FIG. 5A*　　*FIG. 5B*

Hydrate Mediated Proton Transfer (1.)

Sodium Bisulfate Monohydrate (solid)  Potassium Chlorate (involatile solid)

The sodium bisulfate anion transfers a proton to a nearby water molecule to form a hydronium cation.

(2.)

Potassium Chlorate (involatile solid)

The hydronium cation is highly mobile and can easily move between the two solid surfaces.

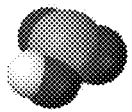
FIG. 7C

FIGURE 13A
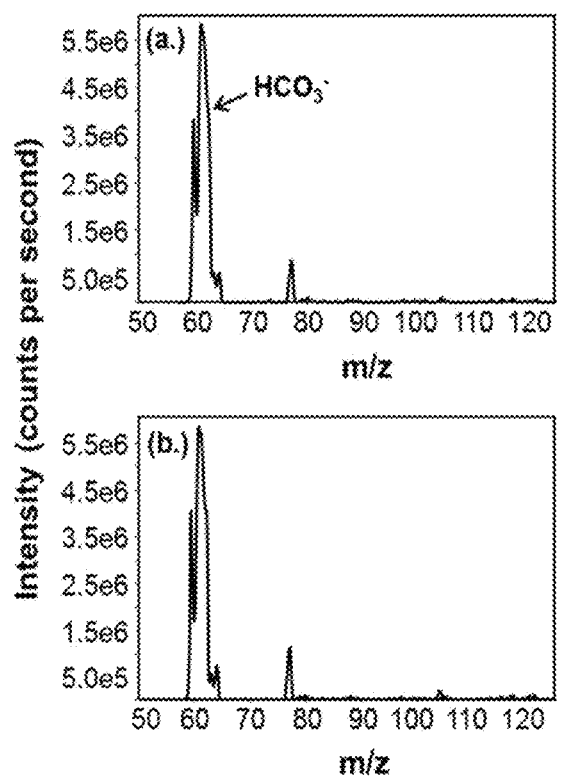
FIG. 13B
FIGURE 13C
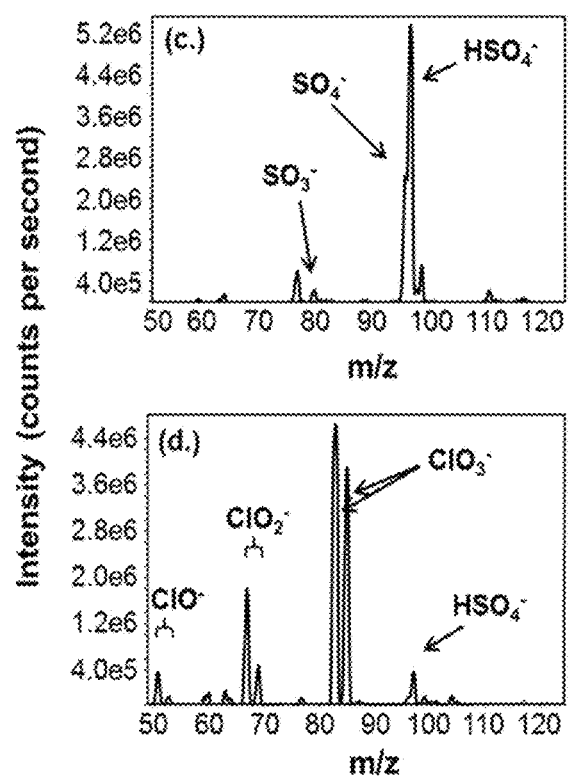
FIG. 13D

REAGENTS FOR ENHANCED DETECTION OF LOW VOLATILITY ANALYTES

REFERENCE TO RELATED APPLICATIONS

The present application claims priority as a continuation application to U.S. patent application Ser. No. 14/679,891, entitled "Reagents for Enhanced Detection of Low Volatility Analytes", filed Apr. 6, 2015, which claims priority to U.S. Provisional Patent Application No. 61/975,275 entitled "Reagents for Enhanced Detection of Low Volatility Analytes", filed on Apr. 4, 2014. The present application is also a continuation in part of U.S. patent application Ser. No. 15/435,733, entitled "Reagents For Oxidizer-Based Chemical Detection", filed on Feb. 17, 2017, which is a division of U.S. patent application Ser. No. 13/948,423 (now U.S. Pat. No. 9,588,095), entitled "Reagents For Oxidizer-Based Chemical Detection", filed Jul. 23, 2013, which claims priority to U.S. Provisional Patent Application No. 61/806,636 entitled "Novel Reagents For Oxidizer-Based Explosives For Use With Ambient Ionization Technology", filed Mar. 29, 2013. The U.S. patent application Ser. No. 15/435,733, entitled "Reagents For Oxidizer-Based Chemical Detection", filed on Feb. 17, 2017, is also a continuation in part of U.S. patent application Ser. No. 13/832,905 (now U.S. Pat. No. 9,891,193), entitled "Reagent Impregnated Swipe For Chemical Detection", filed Mar. 15, 2013, which claims priority to U.S. Provisional Patent Application No. 61/674,980 entitled "Reagent Impregnated Swipe For Thermal Desorption Release And Chemical Detection With Ambient Ionization Technology", filed Jul. 24, 2012. Each of these applications is herein incorporated by reference in its entirety.

GOVERNMENT RIGHTS

This invention was made with Government support under Contract No. FA8721-05-C-0002 awarded by the U.S. Air Force. The Government has certain rights in the invention.

BACKGROUND OF INVENTION

The technical field of this invention is spectrometry, e.g., ion mobility spectrometry and the like, and in particular to methods and reagents that can enhance the ionization of low volatility analytes.

The threats posed by concealed explosives and the intentional release of toxic chemicals continue to drive improvements in ways to detect these threats as a means to protect the public. One technique used to aid in this mission involves identification of the threat molecule by first ionizing it, and then detecting whether the threat molecule (analyte) is present. Ion mobility spectrometry (IMS), differential mobility spectrometry (DMS), field asymmetric ion mobility spectrometry (FAIMS), and mass spectrometry (MS) are all methods used to identify molecules that first require ionization. Given the importance of these techniques to public safety, considerable effort has been devoted to develop the best means to collect the sample from the environment, present the sample to the instrument, and to also ionize it efficiently and, if possible, selectively in order to provide the greatest detection capability. In almost all instances, the ionization is achieved at ambient-pressure using a technique called ambient-pressure ionization (API) (also sometimes called atmospheric-pressure chemical ionization). Because the ionization occurs in the gas phase through ion-molecule collisions, it is usually essential that the analyte is first vaporized to be present in the gas phase.

However, many of the explosive and chemical threats have low vapor pressure and exist as traces of solid particulates or thin films on surfaces, and thus the most common way to collect the sample requires a swipe or swab substrate which provides a physical mechanism to both collect and preconcentrate the sample off the contaminated surface for subsequent presentation to the ionization space of the detection instrument. The substrate media, or "swipe", containing the collected sample can be used to present the sample to the ionization instrument in one of two ways. In the first method, the swipe can be extracted using a solvent to selectivity dissolve the collected analyte into a solvent liquid, which is then presented to the ionization space of the instrument via a process called electrospray ionization. (See U.S. Pat. Nos. 8,513,596; 5,157,260; and 5,756,994, for examples of this approach). This requires extraction, dissolution, and injection steps and, although effective, is not practical in field settings. The alternative, and currently preferred, method is to heat the swipe to desorb the target chemical into the vapor phase for subsequent ionization and detection.

In a typical API system, a swipe or swab substrate is positioned in a thermal desorber located on the inlet side of the detection system. Thermal heating of the solid analyte particles on the swipe induces a solid-to-vapor phase transition and releases the analyte molecules as a vapor, usually guided into the sensor inlet by a carrier gas, and ionization occurs in the vapor phase. Properties of commercially-available swipe media have been optimized over the years for increased efficiency of particle collection from surfaces (mechanical or electrostatic), efficient transfer and release of analyte into the chemical sensor, thermal stability, and low chemical background of the substrate. Prior art exists in the patent literature on different embodiments of sampling swipes (e.g., US2006-0192098; EP1844189 and WO2007-066240). See also, commonly-owned U.S. patent application Ser. No. 13/832,905 filed entitled "Reagent Impregnated Swipe for Thermal Desorption Release and Chemical Detection with Ambient Ionization Techniques," which discloses reagents that are chemically embedded in the swipe material for interaction with the analyte.

One area where such an approach may be beneficial is for detection of materials such as the sodium and potassium salts of chlorate and perchlorate, which do not have appreciable vapor pressures to allow for sensitive detection at desorption temperatures less than 250° C. Reagents that convert these compounds to more volatile compounds at temperatures less than 250° C. can thus provide one means to improve performance of API-based detection systems and/or allow for operation at lower temperatures.

SUMMARY OF THE INVENTION

In one aspect, the use of volatilization reagents is disclosed for improved detection of inorganic oxidizers such as but not limited to chlorates, perchlorates, permanganates, dichromates, and osmium tetraoxides. In some embodiments, detection methods are disclosed whereby a reagent can transfer a proton to the anion (i.e., chlorate, perchlorate, etc.) of an inorganic salt analyte, forming an acid (i.e., chloric acid, perchloric acid) that is easier to detect by a mechanism whereby the acidified reagent is more easily vaporized, and hence, more easily detected. Concurrently, the anion of the acid forms a new salt with the cation released from the salt that was acidified. In another aspect of the invention, a class of reagents is disclosed that can carry out this method. In various embodiments, these reagents can be embedded in a swipe or other substrate, as a liquid infused via nebulizer, or by other practical means for introduction.

The volatilization reagents described herein offer distinct advantages over current approaches and offer improved detection of inorganic oxidizers without increasing hardware complexity. The primary challenge for detection of inorganic oxidizers is the low vapor pressure of many of these materials. Low volatility analytes such as inorganic oxidizer salts (i.e., potassium chlorate) currently require thermal desorption or ionization source temperatures on the higher end of, or even exceeding, what is desirable for current detection devices, i.e. temperatures exceeding 350° C. Achieving such high temperatures is an engineering challenge specifically in smaller, field portable systems where size, weight and power must be minimized and long thermal cycling reduces sample throughput. Such high temperatures can cause destruction of other more delicate analytes of interest (such as organic molecules) that may be coexistent in the analyzed sample. High temperatures can also increase the amount of background signal observed in a detection device, which decreases the quality of quantitative measurements.

The invention discloses reagents offering indirect detection of the analyte at lower temperatures. Take for example the inorganic oxidizer potassium perchlorate $KClO_4$, the detection of which is limited using conventional atmospheric pressure chemical ionization at temperatures less than about 350° C. The use of an acidic reagent is disclosed to chemically transform the anion of the oxidizer (e.g. perchlorate, $ClO_4^-$) into a much more volatile acid (e.g. perchloric acid, $HClO_4$). In this case, the perchloric acid has a much higher vapor pressure than its parent oxidizer salt, and is itself easily ionized to create $ClO_4^-$ which is observed in negative ion detection mode. The acidic volatilizing reagent also supplies an anion (e.g. $SO_4^{2-}$) that can associate with cations of the oxidizing salt (e.g. $K^+$), providing charge balance and thermodynamic stability. The useful result of this concerted chemistry is increased availability of detectable anions (e.g. perchlorate) in the gas phase.

The reagents may be delivered by any reasonable method depending on the physical state of the reagent(s), as either solid, liquid or vapor. The introduction method may be via the solid state on or in a swipe or other substrate, liquid infused via nebulizer (inside or outside of an instrument), or by other practical means for introduction. In each of these embodiments, the objective is to broaden the range, type, and performance of volatilization reagents which in turn allows for the API detection of a wider range of threat chemicals with greater signal intensities and better precision at lower temperatures. This advantage is important as the range of threats increases.

In one aspect, the volatilization reagents of this invention are specific for detection of inorganic oxidizers that will increase the amount of characteristic anions from the analyte entering the gas phase for subsequent detection. The presence of the volatilization reagent has the net effect of increasing the amount of signal detected from an analyte at a given temperature and allows for improved detection of these analytes at lower API source temperatures. Although volatilization reagents have been disclosed previously for other applications, there have been no previous disclosures of this acidic volatilization reagent approach for detection of inorganic oxidizers by API methods.

In another aspect of the invention, acidic volatilization reagents and methods of use are disclosed for detection of oxidizers. (The terms "volatilization reagent and "evaporative reagent are used interchangeably herein.) Through co-introduction of the acidic reagent and the target analyte into the thermal desorption space of an instrument, the two can communicate with one another resulting in the protonation of the analyte's anion to form an acid molecule. The overall reaction is generally described as a salt methathesis reaction, where the acidic reagent and the analyte salt effectively swap cations and anions with each other. The desired outcome of this reaction is a new acid, containing the anion of the originating analyte salt, where the acid is more volatile and hence easier to detect than the originating salt.

Thus, reaction schemes are disclosed in which a proton-containing reagent can react with an ionic analyte by exchanging the analyte's cation with a proton, and the corresponding association of the analyte's displaced cation with the reagent's anion, resulting in increased volatility of the analyte's protonated anion which thereby increases its detectability in an ion detection apparatus. The proton-containing or "acidic" reagent compound can be a strong acid such as hydrochloric acid or sulfuric acid. Alternatively, the reagent compound can be a weak acid such as acetic acid, trifluoroacetic acid, or formic acid. In other embodiments, the acidic reagent compound can be an acidic salt such as the alkali-containing acidic salts sodium bisulfate, potassium bisulfate, or sodium biphosphate. The acidic reagent compound can be in the solid or liquid phase. The acidity of the reagent, relative to that of the analyte, can also be tailored to provide reaction selectivity when compared to other analytes In practice, one or more than one ion can be formed for detection from interaction between the reagent and analyte (s). Analytes include, but are not limited to ionic components of explosives such as salts of chlorate, perchlorate, permanganate, dichromate, and osmium tetraoxide.

The methods of the present invention can be practiced where the reaction between the chemical (i.e., the acidic reagent) and the analyte occur on a dry, chemically treated collection swipe pre-impregnated with the acidic reagent (i.e. an acidic salt). In some embodiments, in addition to the reagent, an additional thermally labile hydrated salt can be incorporated into the pretreated swipe as an additional source of water upon heating. In such cases, the solid hydrate can provide an additional source of water. In certain embodiments, an aqueous solution of the thermally labile hydrated salt preferably exhibits a pH between about 5 and 9. One example of a thermally labile hydrated salt reagent is sodium thiosulfate pentahydrate. In some embodiments, the swipe can contain both sodium bisulfate as a reagent and sodium thiosulfate pentahydrate as a source of water.

In other embodiments, the reaction between the acidic reagent and the analyte can occur in the liquid phase after application of a liquid reagent-containing solution to a surface containing the analyte. For example, the liquid-phase acidic reagent can be applied directly to a swipe containing the analyte. The liquid-phase acidic reagent can also be applied within an ion detection apparatus prior to or during the heating of the analyte containing surface.

In another aspect of the invention, methods are disclosed for detection of an analyte molecule, X, potentially present in a sample, wherein the method includes, but is not limited to, treating the sample with an evaporative reagent (e.g., an acidic reagent) to form a higher vapor pressure analog of the analyte if present in the sample, and subjecting the treated sample to mass spectrometry, whereby the presence of X in the sample can be deduced. The thus treated sample can then be subjected to mass spectrometry, e.g. ion mobility spectrometry or the like.

The method can further include associating the evaporative reagent with a swipe prior to sample collection and then using the swipe to obtain a sample. In certain embodiments, the reagent can interact with the analyte (if present in the sample) either prior to desorption in a detection instrument or after it is released into a carrier gas along with any target analyte molecules captured by the swipe following desorption.

Evaporative reagents according to some embodiments of the invention can include at least one acid reagent selected from the group of sulfuric acid, hydrochloric acid, hydrofluoric acid, hydroiodic acid, hydrobromic acid, nitric acid, oxalic acid, water, hydrogen sulfate, phosphoric acid, formic acid, benzoic acid, acetic acid, propionic acid, or other organic acids of the form R—COOH where R is an alkyl, substituted alkyl, aryl, or substituted aryl group or at least one other cation donor.

In some embodiments, an acidic evaporative reagent employed for enhanced detection of an analyte of interest can be a polymeric and/or sulfonic organic acid. By way of example, the acidic reagent can be a polymeric sulfonic acid, such as perfluorinated sulfonic acid. By way of example, the perfluorinated sulfonic acid can be a sulfonated tetrafluoroethylene based fluoropolymer-copolymer such as Nation®. Another example of a suitable polymeric organic acid is polystyrene sulfonic acid.

In some embodiments, the acidic evaporative reagent can be a hydrated acidification reagent in solid or liquid phase. By way of example, the hydrated acidification reagent can be a hydrated sulfonate- or sulfate-containing acid, such as sodium bisulfate monohydrate (e.g., in solid phase).

In certain embodiments the evaporative reagent can donate a cation other than a proton. For example, the evaporative reagent can include a quaternary ammonium cation donor selected from the group of quaternary ammonium salts that can donate a cation having the formula, N—R1-R2-R3-R4, where R1, R2, R3 and R4 are hydrogen or straight or branched alkyl, preferably lower alkyl, groups.

In some embodiments, the evaporative reagent can be an acidic salt such as the alkali-containing acidic salts sodium bisulfate, potassium bisulfate, or sodium biphosphate. It can also be preferable in some instances to employ hydrated acidic salts, in which there are one or more water molecules associated with at least some of the salt molecules.

In some instances, the methods and reagents of the present invention can be further enhanced by the addition of water-containing reagents or co-reagents. The presence of water typically increases the effectiveness of the reactions disclosed herein. For example, sodium bisulfate can be employed as a monohydrate and can essentially supply its own water. To supply even more water to assist the reaction, a solid compound (e.g. sodium thiosulfate pentahydrate, $Na_2S_2O_3.5H_2O$) can be introduced to the swipe material alongside one or more acidic volatilization reagents.

In a related aspect, a swipe for detection of an analyte molecule is disclosed, which includes a substrate configured to collect a sample for analysis, and an acidic reagent (e.g., a proton-containing acidic reagent) that is associated with the substrate and is configured to react with the analyte, if present in the sample, so as to generate a higher vapor pressure analog of the analyte. The acidic reagent can be associated with the substrate via a variety of mechanisms, such as physical entrainment, covalent and/or non-covalent bonds.

The acidic reagent can comprise any of the reagents disclosed above, or others apparent to those having ordinary skill in the art in view of the present teachings. By way of example, in some embodiments, the acidic reagent can be a polymeric and/or sulfonic organic acid, such as a polymeric sulfonic acid (e.g., solid sodium bisulfate monohydrate). In some embodiments, the acidic reagent can comprise an acidic salt, such as an alkali-containing acidic salt. Some example of suitable alkali-containing salts include, without limitation, sodium bisulfate, potassium bisulfate, or sodium biphosphate. In some embodiments, the acidic salt further comprises a thermally labile hydrated salt that can provide an additional source of water upon heating. By way of example, the thermally labile hydrated salt can be sodium thiosulfate pentahydrate.

In a related aspect, a method for detection of an analyte molecule in a sample is disclosed, which comprises applying an acidic evaporative reagent in liquid phase to a surface suspected of containing an analyte, whereby generating a higher pressure analog of the analyte is present on the surface, and thermally desorbing the higher pressure analog for analysis with mass spectrometry. The acidic reagent reacts with the analyte in liquid phase after application thereof to the surface to generate the higher vapor pressure analyte. The liquid-phase acidic reagent can comprise a reagent-containing solution. In some embodiments, the liquid-phase acidic reagent is applied directly to a swipe surface suspected of containing the analyte. In some embodiments, the liquid-phase acidic reagent is applied within an ion detection apparatus (e.g., a mass spectrometer, such as an ion mobility spectrometer or a differential mobility spectrometer) prior to or during the heating of the analyte containing surface. The acidity of the reagent relative to that of the analyte can be tailored to provide reaction selectively when compared to other analytes. In some embodiments, the acidic evaporative reagent can be a polymeric organic acid and/or a hydrated solid state acid. Generally speaking, methods for detection of an analyte, X, potentially present in a sample, are disclosed including the steps of treating the sample with an acidic evaporative reagent having a pKa of less than 2.5, or less than 2, or less than 0, or less than −2 to form a higher vapor pressure analog of the analyte if present in the sample, and subjecting the treated sample to mass spectrometry, whereby the presence of X in the sample can be deduced. The acidic evaporative reagent can be one or more of a polymeric sulfonic organic acid, such as for example, a polystyrene sulfonic acid or a perfluorinated sulfonic acid, such as for example, a sulfonated tetrafluoroethylene based fluoropolymer-copolymer. In certain embodiments, the acidic evaporative reagent can be a hydrated acidification reagent or more specifically a hydrated sulfonate- or sulfate-containing acid, such as for example, sodium bisulfate monohydrate.

The methods disclosed herein can be practiced by subjecting the treated sample to mass spectrometry further comprises subjecting the treated sample to ion mobility spectrometry or differential mobility spectrometry. The methods can also be practiced by associating the acidic evaporative reagent with a swipe prior to sample collection and then using the swipe to obtain a sample. The reagent can interact with the analyte if present in the sample either prior to desorption in a detection instrument or after it is released into a carrier gas along with any target analyte molecules captured by the swipe following desorption. The reagent can be a solid or liquid phase reagent applied to a substrate prior to collection of a sample for analysis.

Alternatively, the reaction between the acidic reagent can occur in the liquid phase after application of a liquid-phase acidic reagent to a surface containing the analyte, for example by applying a reagent-containing solution to a swipe which has been used to collect a sample or by applying the liquid-phase acidic reagent within an ion detection apparatus prior to or during the heating of the sample. The acidity of the reagent, relative to that of the analyte, can be tailored to provide reaction selectivity when compared to other analytes.

The methods disclosed herein can also be practiced by applying a co-reagent capable of releasing water or more specifically a thermally labile hydrate, such as for example, sodium bisulfate monohydrate. Thus, methods for detection of an analyte molecule, X, potentially present in a sample, are disclosed including the steps of treating the sample with an acidic evaporative reagent and a co-reagent capable of releasing water to form a higher vapor pressure analog of the analyte if present in the sample, and subjecting the treated sample to mass spectrometry, whereby the presence of X in the sample can be deduced. The co-reagent can be a thermally labile hydrate, such as for example, sodium bisulfate monohydrate, capable of releasing water upon heating. These methods can be practice together with an acidic reagent is selected from the group of polymeric organic acids and polymeric sulfonic acids. In the case of polymeric sulfonic acids, reagent can include one or more of a polymeric sulfonic organic acid, such as for example, a polystyrene sulfonic acid or a perfluorinated sulfonic acid, such as for example, a sulfonated tetrafluoroethylene based fluoropolymer-copolymer. Alternatively, the acidic evaporative reagent can include a hydrated acidification reagent, or more specifically, a hydrated sulfonate- or sulfate-containing acid, such as for example, solid sodium bisulfate monohydrate. The acidity of the reagent, relative to that of the analyte, can be tailored to provide reaction selectivity when compared to other analytes. The step of subjecting the treated sample to mass spectrometry can further include subjecting the treated sample to ion mobility spectrometry or differential mobility spectrometry.

The acidic reagent and/or the co-reagent can be a solid or liquid phase reagent applied to a substrate, such as a swipe, prior to collection of a sample for analysis. The reagent can interact with the analyte if present in the sample either prior to desorption in a detection instrument or after it is released into a carrier gas along with any target analyte molecules captured by the swipe following desorption. In certain embodiments, the reaction between the acidic reagent and/or the coreagent can occur in the liquid phase after application of a liquid-phase acidic reagent and/or the co-reagent to a surface containing the analyte, for example by applying a solution containing the reagent and/or the co-reagent to a swipe which has been used to collect a sample or by introducing the liquid-phase reagent and/or co-reagent into an ion detection apparatus prior to or during the heating of the sample.

In another aspect, swipes are disclosed for detection of an analyte molecule according to the various methods described herein, For example, the swipe can include a substrate configured to collect or receive a sample for analysis, and an acidic evaporative reagent selected from the group of polymeric organic acids and polymeric sulfonic acids associated with the substrate configured to react with an analyte, if present in the sample, so as to generate a higher vapor pressure analog of the analyte.

The swipes can include one or more of a polymeric sulfonic organic acid, such as for example, a polystyrene sulfonic acid or a perfluorinated sulfonic acid, such as for example, a sulfonated tetrafluoroethylene based fluoropolymer-copolymer. The swipe can further include a thermally labile hydrated salt associated with the substrate in solid or liquid form that can provide an additional source of water upon heating. For example, the thermally labile hydrate can include sodium thiosulfate pentahydrate.

In yet another aspect, swipes are disclosed for detection of an analyte molecule according to the methods described herein. The swipe can include a substrate configured to collect or receive a sample for analysis, and an acidic reagent and a co-reagent capable of releasing water associated with the substrate and configured to react with an analyte, if present in the sample, so as to generate a higher vapor pressure analog of the analyte. The co-reagent can be a thermally labile hydrate, such as for example, sodium bisulfate monohydrate, capable of releasing water upon heating. The acidic reagent is selected from the group of polymeric organic acids and polymeric sulfonic acids. In the case of polymeric sulfonic acids, the reagent can include one or more of a polymeric sulfonic organic acid, such as for example, a polystyrene sulfonic acid or a perfluorinated sulfonic acid, such as for example, a sulfonated tetrafluoroethylene based fluoropolymer-copolymer. Alternatively, the acidic evaporative reagent can be a hydrated acidification reagent, or more specifically, a hydrated sulfonate- or sulfate-containing acid, such as for example, solid sodium bisulfate monohydrate.

In certain embodiments, the acidic reagent and/or co-reagent can be applied to the swipe prior to, or after, collection of a sample. The co-reagent can be a thermally labile hydrate, such as for example, sodium bisulfate monohydrate, capable of releasing water upon heating. Alternatively, the acidic reagent is selected from the group of polymeric organic acids and polymeric sulfonic acids. The reagent can be one or more of a polymeric sulfonic organic acid, such as for example, a polystyrene sulfonic acid or a perfluorinated sulfonic acid, such as for example, a sulfonated tetrafluoroethylene based fluoropolymer-copolymer. Alternatively, the acidic evaporative reagent can include a hydrated acidification reagent, or more specifically, a hydrated sulfonate- or sulfate-containing acid, such as for example, solid sodium bisulfate monohydrate.

In one aspect, an acidic evaporative reagent according to the present teachings (e.g., an organic polymer acid) can be delivered to an ion detection apparatus, such as, a mass spectrometer, as a liquid infused via a nebulizer.

The invention is useful in a wide range of ion detection apparatus, such as an ion mobility spectrometry, differential mobility spectrometers, or mass spectrometers.

BRIEF DESCRIPTION OF THE DRAWINGS

The appended drawings have been included herein so that the above-recited features, advantages and objects of the invention will become clear and can be understood in detail. These drawings form a part of the specification. It is to be noted, however, that the appended drawings should not be considered to limit the scope of the invention.

FIG. 3 illustrates representative net reactions according to some embodiments of the invention. Reactions (a) through (f) show volatilization of chlorate and perchlorate salts using: hydrochloric acid (a, b), sulfuric acid (c, d) and sodium bisulfate (e, f). In each case, a more volatile acid, chloric ($HClO_3$) or perchloric ($HClO_4$) acid is generated from the relatively involatile analyte salt. Reaction (g) shows how sodium thiosulfate pentahydrate ($Na_2S_2O_3.5H_2O$) liberates water molecules in the presence of applied heat ($\Delta q$). Water molecules liberated by reaction (g) help facilitate reactions of type (e) and (f).

FIGS. 5A-5B illustrates a 3D model of anhydrous (5A) and hydrated (5B) sodium bisulfate, respectively.

FIGS. 7A-7C illustrate the transfer of a proton from a hydrated acidic salt (sodium bisulfate monohydrate) to solid potassium chlorate via protonation of a nearby free and mobile water molecule.

FIGS. 13A-13D are graphs of negative ion TD APCI mass spectra all at a thermal desorption temperature of 150° C. FIG. 13A is a graph of the blank background spectrum. FIG. 13B is a graph of 0.5 µg $KClO_3$(s). FIG. 13C is a graph of the background subtracted 150 µg $NaHSO_4.H_2O$(s). FIG. 13D is a graph of the background subtracted of 0.5 µg $KClO_3$(s) combined with 150 µg $NaHSO_4.H_2O$(s).

DETAILED DESCRIPTION

Figure 1:
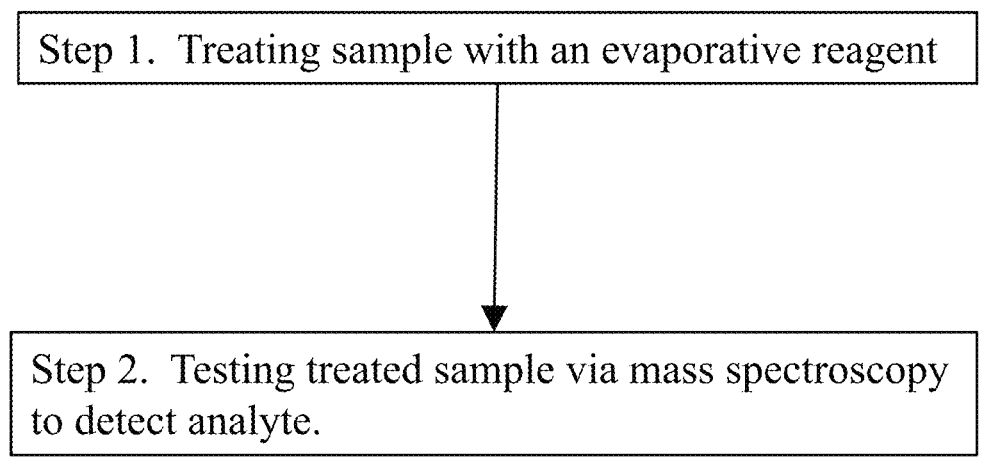
FIG. 1 is a flow diagram depicting various steps in a method according to an embodiment of the present invention for detection of an analyte molecule of interest in a sample.

Certain exemplary embodiments will now be described to provide an overall understanding of the principles of the structure, function, manufacture, and use of the devices and methods disclosed herein. One or more examples of these embodiments are illustrated in the accompanying drawings. Those skilled in the art will understand that the devices and methods specifically described herein and illustrated in the accompanying drawings are non-limiting exemplary embodiments and that the scope of the present invention is defined solely by the claims. The features illustrated or described in connection with one exemplary embodiment can be combined with the features of other embodiments. Such modifications and variations are intended to be included within the scope of the present invention.

All publications, patents and patent applications cited herein, whether supra or infra, are hereby incorporated by reference in their entirety. As used in this specification and the appended claims, the singular forms "a," "an," and "the" include plural references unless the content clearly dictates otherwise. The terms used in this invention adhere to standard definitions generally accepted by those having ordinary skill in the art. In case any further explanation might be needed, some terms have been further elucidated below.

The term "about," as used herein, refers to variations in a numerical quantity that can occur, for example, through measuring or handling procedures in the real world; through inadvertent error in these procedures; through differences in the manufacture, source, or purity of compositions or reagents; and the like. Typically, the term "about" as used herein means greater or lesser than the value or range of values stated by 1/10 of the stated values, e.g., ±10%. For instance, a concentration value of about 30% can mean a concentration between 27% and 33%. The term "about" also refers to variations that would be recognized by one skilled in the art as being equivalent so long as such variations do not encompass known values practiced by the prior art. Each value or range of values preceded by the term "about" is also intended to encompass the embodiment of the stated absolute value or range of values. Whether or not modified by the term "about," quantitative values recited in the claims include equivalents to the recited values, e.g., variations in the numerical quantity of such values that can occur, but would be recognized to be equivalents by a person skilled in the art.

The terms "polymeric acids," "polymeric organic acids," and polymeric sulfonic acids" are used herein consistent with their standard use in the art. A polymeric acid refers to a polymer having one or acidic functional groups. In certain preferred embodiments, the majority, or more than 75 percent, or all of the repeat units include an acid moiety capable of donating a proton. The repeat units needn't all be identical. The repeating subunits of the polymer can be bonded together to form a linear, a branched or a cyclic structure.

The term "polymeric organic acid" as used herein, is intended to encompass molecules (i) having one or more repeat units that are covalently linked together, (ii) largely comprising elements that occur in natural materials, namely carbon, hydrogen, oxygen, and nitrogen, and (iii) can donate a proton to another molecule. In some embodiments, the polymeric organic acids of the invention have at least some carbon atoms in their backbone. In certain preferred embodiments, the majority, or more than 75 percent, or all of the repeat units include an acid moiety capable of donating a proton. The repeat units needn't all be identical. The repeating subunits of the polymer can be bonded together to form a linear, a branched or a cyclic structure.

The term "polymeric inorganic acid" is typically used to describe analogs of polymeric organic acids having atomic backbones completely free of carbon, such as polysiloxanes (silicon-oxygen backbones), polyphosphates (phosphorous and oxygen backbones), and polysilanes (all silicon backbones). In some instance, such molecules can have an equivalent effect in inducing evaporation of low volatility analytes. In certain preferred embodiments, the majority, or more than 75 percent, or all of the repeat units include an acid moiety capable of donating a proton. The repeat units needn't all be identical. The repeating subunits of the polymer can be bonded together to form a linear, a branched or a cyclic structure.

The term "polymeric sulfonic acid" as used herein, is intended to encompass molecules (i) having one or more repeat units that are covalently linked together, (ii) include sulfur and (iii) can donate a proton to another molecule. Similarly to polymeric organic acids, in certain preferred embodiments the majority, or more than 75 percent, or all of the repeat units include an acid moiety capable of donating a proton. Again, the repeat units needn't all be identical and the repeating subunits of the polymer can be bonded together to form a linear, a branched or a cyclic structure.

In some embodiments, the molecular weights of the polymeric organic acids and polymeric sulfonic acids useful herein can range from between 1,000 and 1,000,000 Da, or between 10,000 and 200,000 Da, or between 50,000 and 150,000 DA. In certain embodiments, a variant of polystyrene sulfonic acid having a molecular weight of about 75,000 Da was useful. However, it is understood to those skilled in the art that in certain aspects of this invention is the polymer's ability to act as an acid, that is to say, to donate a proton. Thus by extension any polymer, independent of its molecular weight, which exhibits such properties, is intended to be encompassed.

In some embodiments, the number of repeat units in the polymeric organic acids and polymeric sulfonic acids useful herein can range from about 50 to about 1000 repeat units or between about 100 and about 700 repeat units or between about 200 and about 600 repeat units. In certain embodiments a variant of polystyrene sulfonic acid having about 400 repeat units was useful.

In general, the pKa's of the acidic evaporative reagents (or polymeric acids) useful herein are less than 2.5, or less than 2, preferably less than 0, or in some instances more preferably less than −2. In some embodiments, sulfonic acids, such as benzene sulfonic acid (pKa=−2.8), polystyrene sulfonic acid (pKa=−3), substituted polystyrene sulfonic acids (pKa=−3 to −6) and Nafion™ a perfluorinated sulfonic acid (pKa=−6) have been useful.

In summary, the key aspects of the acidic evaporative reagents are their ability to convert strong oxidizers (chlorate, perchlorate) into their acidic form (chloric acid, perchloric acid), while having both no discernable vapor pressure and chemical stability to >150° C., thus not off-gassing any unwanted vapors into the analysis instrument, thereby allowing the analysis instrument to receive only the acidified oxidizers.

The term "swipe" is used herein in its general sense to mean a vehicle for collection of a sample. Typically in the context of IMS, the swipe is a substrate including a least one of paper, fabric, cloth, fibrous matte, gauze, cellulose, cotton, flax, linen, synthetic fibers and blends of such materials. However, other materials such as ceramic or semiconductor materials can also be used as "swipes" depending upon the analysis scheme.

Mass spectrometry is an analytical process for identifying a compound or compounds in a sample by assessing the molecular weight, chemical composition and structural information based on the mass-to-charge ratio of charged particles. Mass spectrometry is widely considered to have the best specificity of any technique applicable to a broad class of explosive compounds. In general, a sample undergoes ionization to form charged particles as ions; these charged particles are then passed through electric and/or magnetic fields to separate them according to their mass-to-charge ratio. The terms "mass spectrometry" and "spectrometry" are used herein to encompass techniques that produce a spectrum or spectra of the masses of molecules present in a sample. Mass spectrometry includes, but is not limited to, ion mobility spectrometry (IMS), differential mobility spectrometry (DMS), field asymmetric ion mobility spectrometry (FAIMS), and mass spectrometry (MS), all of which rely upon ionization of the analyte or a complex that includes the analyte. The analysis performed in spectrometry is typically referred to as "mass/charge" analysis, a method of characterizing the ions detected by a spectrometer in terms of their mass-to-charge ratio. The abbreviation m/z is used to denote the quantity formed by dividing the mass number of an ion by its charge number. It has long been called the mass-to-charge ratio although m is not the ionic mass nor is z a multiple or the elementary (electronic) charge, e. Thus, for example, for the ion $C_7H_7^{2+}$, m/z equals 45.5.

The ionization process can be performed by a wide variety of techniques, depending on the phase (solid, liquid, gas) of the sample and the efficiency of the target analyte(s) in question. Some examples of ion sources can include electron ionization, glow discharge ionization, resonant ionization, field desorption, fast atom bombardment, thermospray, desorption/ionization on silicon, atmospheric pressure chemical ionization, spark ionization, inductively coupled plasma ionization, secondary ionization by sputtering ion beams off the target's surface, and thermal ionization.

Ambient-pressure ionization, collision-induced ionization, and atmospheric-pressure chemical ionization refer to a characterization techniques in which picogram to microgram quantities of an analyte can be analyzed. The process generally refers to a chemical sample that is introduced into an ionization region as either a solid, liquid, or gas. In the ionization region, the analyte is in contact with other gases and ions that are part of the ionization region. Additional ions are produced through the collision of the analyte molecules with ions within the ionization reagent that are present in the ion source, electro-magnetic device. Inside the ion source, the ionization reagent is present in large excess compared to the analyte. Electrons and/or ions entering the source will preferentially ionize the ionization reagent. Collisions with other ionization reagent molecules will induce further ionization, creating positive and/or negative ions of the analyte. The ions are drawn into the spectrometer by either a carrier gas or focused into a beam by an electromagnet, then separated into individual beams based on the mass/charge ratio of the ions. The ion beams are separated in a mass spectrometer and collected either sequentially in a single detector or simultaneously in a set of multiple detectors to yield isotopic ratios. Highly accurate results require that sample cross-contamination be minimized.

The traditional methods for explosives detection usually involve wiping the ambient surface with a special material wipe followed by thermal desorption/gas phase ionization of the explosive compounds in the presence of an ionization reagent. The performance of a detection approach such as this depends, in part, on the efficiency with which the explosive compound is transferred from the swipe into the ionization region of the analysis instrument during the desorption step. It is therefore desirable to maximize this efficiency for explosive compounds which have low vapor pressures.

The terms "desorption," "desorb" and "desorbing" as used herein refer to technology of increasing the volatility of molecules, for example target analytes, such that they can be removed (separated) from the solid. Thermal desorption is not incineration, but uses heat and a flow of inert gas to extract volatile and semi-volatile organics retained in a sample matrix or on a sorbent bed. The volatilized compounds are then either collected or thermally destroyed.

In certain embodiments, the reagents of the present invention are low volatility compounds. The terms "low volatility" and "low vapor pressure" as used herein are intended to describe compositions that do not readily evaporate or sublimate at room temperature (e.g., at about 25° C.). Typically such low volatility compositions are solids or viscous liquids and have a vapor pressure at room temperature of less than 1 Torr, or more typically less that $10^{-1}$ Torr. In some preferred embodiments, the low volatility reagents of the present invention can have a vapor pressure at room temperature of or less that $10^{-2}$ Torr or, more preferably, less that $10^{-3}$ Torr.

With reference to flow chart of FIG. 1, in some embodiments, a method for detection of an analyte molecule potentially present in a sample, e.g., inorganic oxidizers such as chlorates and perchlorates, is disclosed that includes treating the sample with an evaporative reagent to form a higher vapor pressure analog of the analyte if present in the sample (step 1). The treated sample can then be subjected to mass spectroscopy to detect the analyte, if present in the sample (step 2). The evaporative reagent can be an acidic volatilization reagent. For example, in some embodiments, the acidic volatilization reagent can be a polymeric organic acid, such, a polymeric sulfonic acid. In some embodiments, the acidic volatilization reagent can be a hydrated solid state acidification reagent, such as, potassium bisulfate monohydrate.

Figure 2:
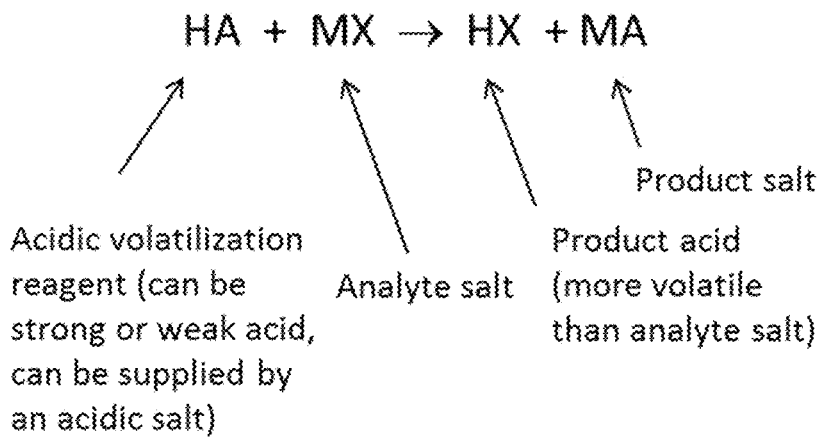
FIG. 2 illustrates an acidic volatilization reagent scheme according to the invention for detection of an analyte salt. The acidic volatilization reagent exchanges its cation (H+) and anion (A−) with the oxidizer analyte salt to create an acid with the same anion as the analyte salt. The volatility of this acid increases the availability of the anion A− for detection in negative ionization mode.

FIG. 2 provides a reagent scheme for detection of an oxidizer in accordance with the present teachings, where an acidic volatilization reagent induces a salt metathesis reaction to increase the availability of an originating salt's anion for detection in a negative ionization mode. The increased vapor pressure of the newly formed acid results in significantly increased detection sensitivity and the ability to perform the detection at lower temperatures. Compounds that can act as acidic volatilization reagents for such enhanced detection include, without limitation, strong acids, weak acids, and acidic salts. An acidic salt can dissociate to release a weak acid via thermal decomposition, or by dissociative solvation in the presence of water. The weak acid released from the acidic salt can then participate in the salt metathesis reaction shown in FIG. 2.

In some instances, the use of a liquid reagent may not be preferable. Additionally, the use of a strong acid (even one that is substantially diluted) may not be desirable or allowed in certain environments. In some instances, the use of solid acidic salts (e.g. sodium bisulfate, $NaHSO_4$) can be the preferred method of providing an acidic reagent. These solids may be applied to existing swipes or introduced during manufacturing of chemically treated swipes. The hydrated form of sodium bisulfate easily vaporizes at low temperatures, liberating the weak acid $HSO_4^-$ which is effective at participating in salt metathesis reactions. The presence of water typically increases the effectiveness of such reactions, and that too can be thermally released from a solid salt. Sodium bisulfate can exist as a monohydrate and can essentially supply its own water. To supply even more water to assist the reaction, a solid compound (e.g. sodium thiosulfate pentahydrate, $Na_2S_2O_3.5H_2O$) can be introduced to the swipe material alongside the acidic volatilization reagent. Numerous such hydrates exist, and when choosing one, three characteristics should be considered. First, the salt of the hydrate should not interfere with the desired salt methathesis reaction. More specifically, it should not compete with the analyte for protons. Secondly, the hydrate should melt and release its hydrated water molecules at temperatures easily attainable in a thermal desorber (i.e., <200° C. or more preferably <150° C.). Lastly, the hydrate should contain as many associated water molecules as possible for the sake of efficiently.

FIG. 3 outlines reactions that are representative of some embodiments of the present invention. More specifically, reactions (a) through (f) show volatilization of chlorate and perchlorate salts using: hydrochloric acid (a, b), sulfuric acid (c, d) and sodium bisulfate (e, f). In each case, a more volatile acid, chloric ($HClO_3$) or perchloric ($HClO_4$) acid is generated from the relatively involatile analyte salt. Reaction (g) shows how sodium thiosulfate pentahydrate ($Na_2S_2O_3.5H_2O$) liberates water molecules in the presence of applied heat ($\Delta q$). Water molecules liberated by reaction (g) help facilitate reactions of type (e) and (f).

The term "hydrate" as used herein is intended to encompass compositions in which there are one or more water molecules associated with at least some of the reagent or co-reagent molecules.

A series of acidic (or other) reagents may be utilized by introduction simultaneously or at discrete times and temperatures to induce selective reactions with expected oxidizers (e.g. reagent A for perchlorate, reagent B for chlorate, reagent C for hydrogen peroxide, reagent D for TATP, reagent E for HMTD). This invention will allow introduction of multiple reagents, if required for more selective detection.

In some embodiments, polymeric organic acids are employed as evaporative reagents for enhanced detection of an analyte molecule present in a sample, for example, for enhanced detection of inorganic oxidizers, such as chlorates and perchlorates. In some embodiments, the polymeric organic acid can have a molecular weight, for example, in a range between 1,000 and 1,000,000 Da, or between 10,000 and 200,000 Da, or between 50,000 and 150,000 DA. Further, in some embodiments, the number of repeating units of the backbone of the polymeric organic acid can range from about 50 to about 1000 repeat units or between about 100 and about 700 repeat units or between about 200 and about 600 repeat units.

Some examples of suitable acidic evaporative reagents include, without limitation, perfluorinated sulfonic acids (e.g., such as but not limited to Nafion™) and polymeric sulfonic acids (e.g., such as but not limited to polystyrene sulfonic acid).

Without being bound to any particular theory, polymeric organic acids, such as perfluorinated sulfonic acids, can act as effective evaporative agents in accordance with some embodiments of the present teachings because (1) their sulfonic functional groups render them extremely acidic, e.g., a pKa of less than 2.5, or less than 2, preferably less than 0, or in some instances more preferably less than −2. (2) these polymeric acids are known to be highly hygroscopic, and typically have water molecules absorbed on their surface that can aid in proton transfer, and (3) these polymeric organic acids can be tailored to release their protons without contributing other materials to the gas phase. As such, in some embodiments, the polymeric organic acids are selected that can enhance the detection of analyte molecules of interest in a very "clean" fashion, i.e., without generating unwanted byproducts. By way of example, this feature can be valuable for explosive trace detection (ETD) as many ETD equipment can manifest strong spectral signals from even small contributions of nuisance chemical byproducts to the gas phase.

In some embodiments, the polymeric organic acids are employed in a solid phase while in other embodiments the polymeric organic acids are employed in liquid phase for enhanced detection of an analyst in a sample.

As discussed above, the intended goal of using acidification reagents for enhanced detection is to efficiently convert inorganic oxidizer salts into their detectable volatile analogs. In some cases, one unintended consequence of this reagent chemistry can be desorption of the acidification reagent itself (or byproducts thereof) during the thermal desorption process in an ETD. This phenomenon has been observed with sodium bisulfate in both the solid and solution state (See, e.g., FIG. 13C). The appearance of new peaks in the IMS or MS is undesirable, as any new peak adds to the 'spectral clutter' and could potentially be confused for threat compounds in some circumstances.

An idealized acidification reagent would convert the anions of inorganic oxidizer salts into their high vapor pressure acidic analogs and make no other contribution to the detectable ensemble of molecules in the gas phase. This could be accomplished by using an acid in which the counter anion (negatively charged component that remains after donating a proton) has a sufficiently low vapor pressure at the thermal desorption temperature. Another strategy involves tethering the counter anion to the substrate of the ETD swipe used for sample gathering.

One advantage polymeric acids according to the present teachings is that the use of such polymeric acids can allow effectively employing both of the above strategies to minimize, and preferably inhibit, contribution to observed spectral clutter. As discussed in more detail below, Applicants have demonstrated the ability of these materials to 'turn on' the acidic enhancement mechanism with little to no contribution to observed spectral clutter.

Figure 4A:
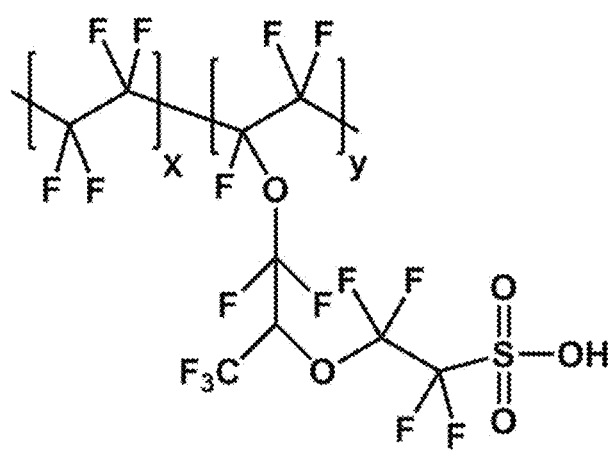
FIGS. 4A-4B illustrate the chemical structures of the polymeric acids Nafion® (FIG. 4A) and polystyrene sulfonic acid (FIG. 4B).
Figure 4B:
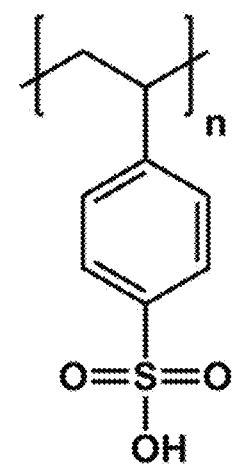

By way of example, FIGS. 4A and 4B show the structures of two polymeric sulfonic acids, namely Nafion™ and polystyrene sulfonic acid, that are suitable for enhanced detection of analytes of interest, and particularly chlorates and perchlorates in accordance with the present teachings. These acids have polymeric backbones that can have arbitrary lengths, from a few subunits to a bulk polymer. Each polymer can have numerous acidic groups branching from the side. While in some embodiments sulfonic acids are used, in other embodiments other acidic functional groups could be utilized. One advantage of these acids is that the sulfonic acid group, which remains behind after the proton ($H^+$) has left the acidic group, is covalently attached to the relatively massive and nonvolatile polymer backbone. This inhibits the ability of the counter anion to enter the gas phase and introduce unwanted spectral clutter.

As discussed above, in some embodiments, solid-state acidification reagents can be used for enhanced detection of analytes of interest. In some such embodiments, the presence of microscopic amounts of free excess water (such as water released from a hydrated crystal upon thermal desorption) can catalyze proton transfer from the acidic reagent to the analyte molecule of interest. Without being bound to any particular theory, the water in hydrate compounds can retain its intact molecular identity. While such water molecules participate in the formation of a crystal lattice, they can be reversibly added or liberated from the crystal under proper conditions.

By way of example, the presence of hydrated or absorbed water on/in a solid-state acidification reagent can help facilitate the proton transfer mechanism between an acidic reagent and a target chlorate or perchlorate salt. Both inorganic and organic solid state acids can exist as hydrates. One such example of an inorganic acid that can exist as a hydrate is sodium bisulfate, shown in FIGS. 5A and 5B, in its anhydrous and hydrated states, respectively.

Figure 6:
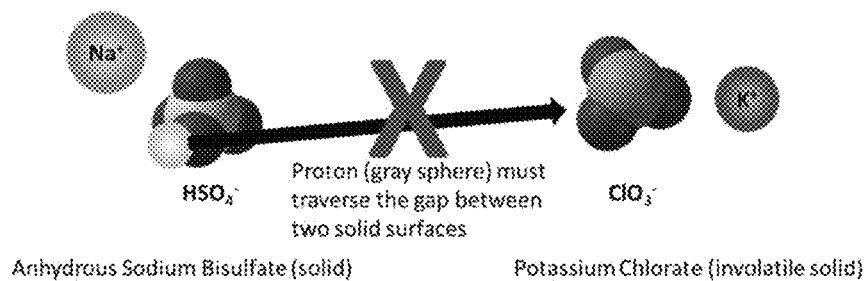
FIG. 6 schematically illustrates that proton transfer between two solids is a relatively inefficient process.

Chemistry in liquid and gas phase, which are inherently mobile phases of matter, typically proceeds more efficiently than solid-state chemistry. For example, as shown schematically in FIG. 6, a solid-state transfer of a proton between the bisulfate anion of anhydrous sodium bisulfate and the chlorate anion of potassium chlorate (a two-body reaction mechanism) can be a relatively inefficient process.

The presence of water greatly enhances the efficiency of proton transfer, because water molecules are highly mobile themselves (in either the liquid or gas phases), and individual water molecules are able to accept extra protons. The protonated water molecules are referred to as hydronium ions. Hydronium ions on their own are quite mobile, and can also rapidly transfer their 'extra' proton to neighboring water molecules.

A solid hydrate (such as sodium bisulfate) can shed water molecules when heated. Thus, in a typical thermal desorption environment, like those found in commercial IMS based ETD equipment, heated hydrates and hygroscopic acids can be surrounded by copious amounts of 'free' water molecules. These free water molecules are in a good position to get protonated by an acidifying reagent and efficiently transfer that proton to a solid potassium chlorate surface some distance away.

Figure 7A:
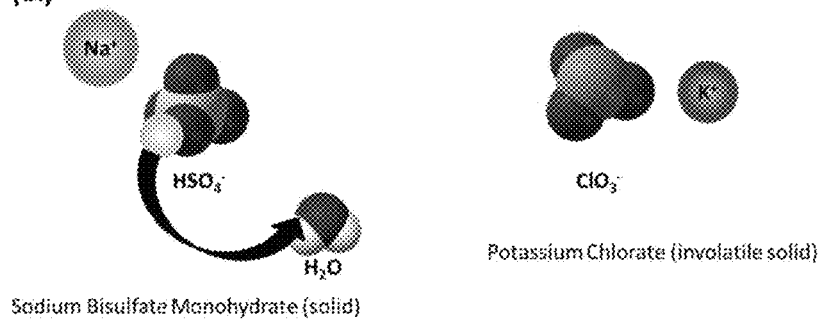
Figure 7B:
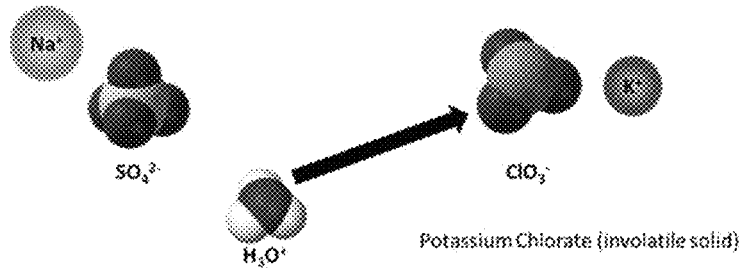

By way of example, FIGS. 7A-7C schematically show how a single water molecule can promote the transfer of the proton between the two solids. While these figures show a single water molecule assisting the proton transfer mechanism, more water molecules (released from other hydrated crystals or from the ambient environment) could also participate in the proton transfer. In these situations, the newly formed hydronium cation would simply transfer its 'extra' proton to a neighboring water molecule in the direction of the potassium chlorate. Water vapor or liquid is an effective conductor of protons, and acts to catalyze the proton transfer reaction.

More specifically, FIG. 7A depicts that the sodium bisulfate transfers a proton from a hydronium cation to a nearby water molecule. The hydronium ion is highly mobile and can readily move between the two solid surfaces to react with the chlorate anion of potassium chlorate, as shown in FIG. 7B. FIG. 7C shows that the hydronium cation donates a proton to the chlorate anion to form chloric acid. The generated chloric acid is highly volatile and hence can be easily detected.

Figure 8:
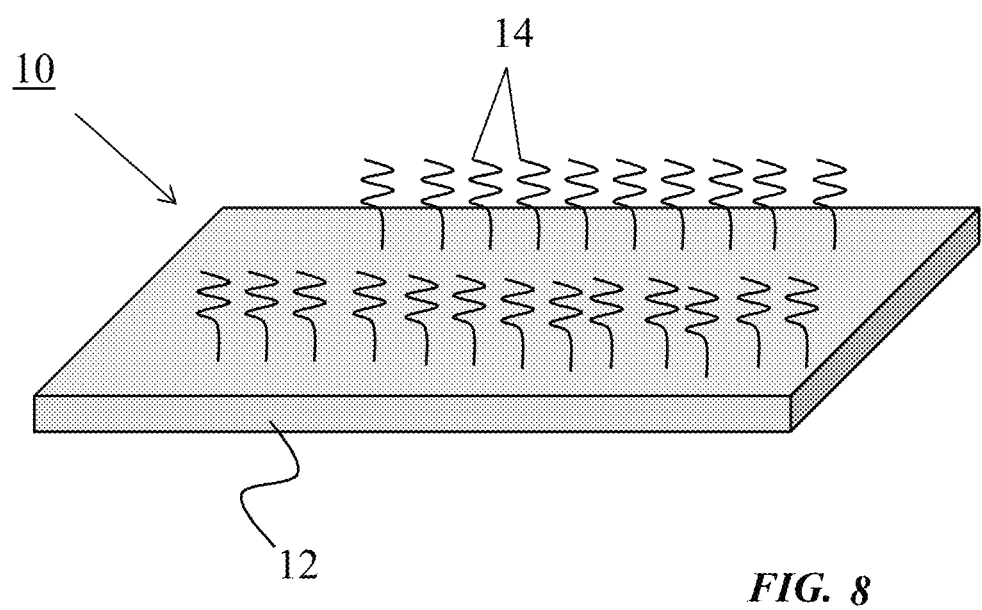
FIG. 8 schematically depicts a swipe according to an embodiment of the present invention.

In some embodiments, swipes for use in detection of analytes of interest, such as, chlorates and perchlorates, are disclosed, which are impregnated with one or more evaporative reagents according to the present teachings. By way of example, FIG. 8 schematically depicts a swipe 10 (also referred to as smear, wipe) according to one embodiment, which includes a substrate 12. The substrate 12 can be formed of a variety of different materials, such as paper, fabric, cloth, fibers, glass, or synthetic material. By of example, in some embodiments, the substrate is fabricated of polyester, muslin, or cotton. The substrate can be preferably formed of a material that can be resistant to chemical degradation during testing in the approximate pH range of 0.1 through 14 to avoid reacting or decomposing. Further information regarding suitable substrates can be found in published U.S. patent application having publication no. 2014/0030816 entitled "Reagent Impregnated Swipe For Chemical Detection," which is herein incorporated by reference in its entirety.

One or more evaporative reagents 14 according to the present teachings, such as those disclosed herein (e.g., polymeric sulfonic acids) is deposited on, embedded in, or otherwise associated with, the substrate 10. The reagents 14 can be associated with the substrate via a variety of different physical and/or chemical mechanisms, such as physical entrainment, non-covalent and/or covalent bonds. In some embodiments, one or more polymeric organic acids can be associated with the substrate by tethering the polymer backbone to the substrate, e.g. via covalent bonds. In some such embodiments, one or more linkers may be employed to tether the polymeric acid to the substrate.

In some embodiments, the swipe 10 can be heat resistant, absorbent and/or chemically resistant at elevated temperatures and can have hydrophilic properties for wetting when using fluid reagents. While in some embodiments, the swipe has a sheet-like structure, in other embodiments, it can have a three-dimensional structure.

Commercial applications include use in all industries involved in chemical detection including but not limited to explosives detection, chemical warfare detection, homeland security, and toxic industrial chemical and pollution monitoring.

EXAMPLES

This invention has been reduced to practice for detection of potassium perchlorate, sodium perchlorate, potassium chlorate, and sodium chlorate via API mass spectrometry. As described earlier, in negative-ion-mode atmospheric pressure chemical ionization, the vaporization (and hence ionization) efficiency of 'bare' oxidizer salts is extremely limited. The examples provided below are only for illustrative purposes, and are not intended to necessarily illustrate the optimal ways of practicing the invention and/or optimal results that may be obtained.

Example 1

Figure 9:
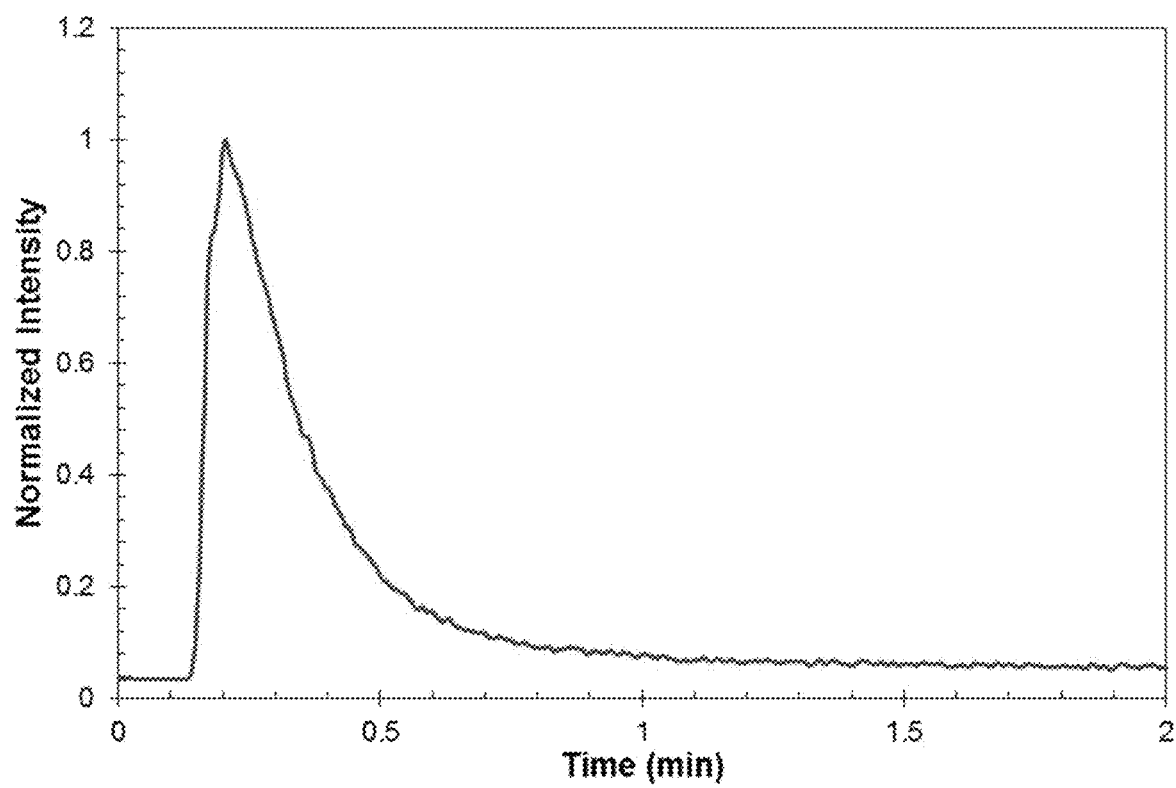
FIG. 9 is a graph of normalized mass spectrometer signal (Y) vs. time (X) obtained by introduction of liquid sulfuric acid (20 µL, 10%) onto a 5 µg sample of dried potassium perchlorate in the desorber unit of a TD APCI mass spectrometer at 150° C.

FIG. 9 illustrates enhancement in observed mass spectrometer ion signal upon addition of an acidic volatizing reagent to an inorganic oxidizer salt. More specifically, FIG. 9 is a graph of normalized mass spectrometer signal (Y) vs. time (X) obtained by introduction of liquid sulfuric acid (20 μL, 10%) onto a 5 μg sample of dried potassium perchlorate in the desorber unit of a TD APCI mass spectrometer at 150° C. In this instance, the mass spectrometer was in MRM mode, measuring the 9983 Da loss channel. Note the dramatic increase in signal at 0.14 minutes when the acidic volatilizing reagent was pre-mixed with the potassium perchlorate sample. In the absence of the acidic volatilizing reagent, no signal was observed from potassium perchlorate at such a low temperature.

Example 2

In another example, in order to increase the amount of free perchlorate anion available for detection, an acidic reagent known to protonate the perchlorate anion ($^{35}ClO_4^-$) was added to a dried potassium perchlorate sample. In these experiments, a liquid reagent, namely 5 μL of 0.01% sulfuric acid (CAS#7664-93-9), was added over a previously dried 5-μg sample of potassium perchlorate on an inert silicon wafer surface. The silicon wafer was then transferred to a thermal desorption unit on a TD APCI source for detection via mass spectrometry. The experimental data presented in FIG. 10 shows the benefits of acidic reagents in terms of both increased mass spectrometer signal and enabling thermal desorption to take place at lower temperatures.

Figure 10:
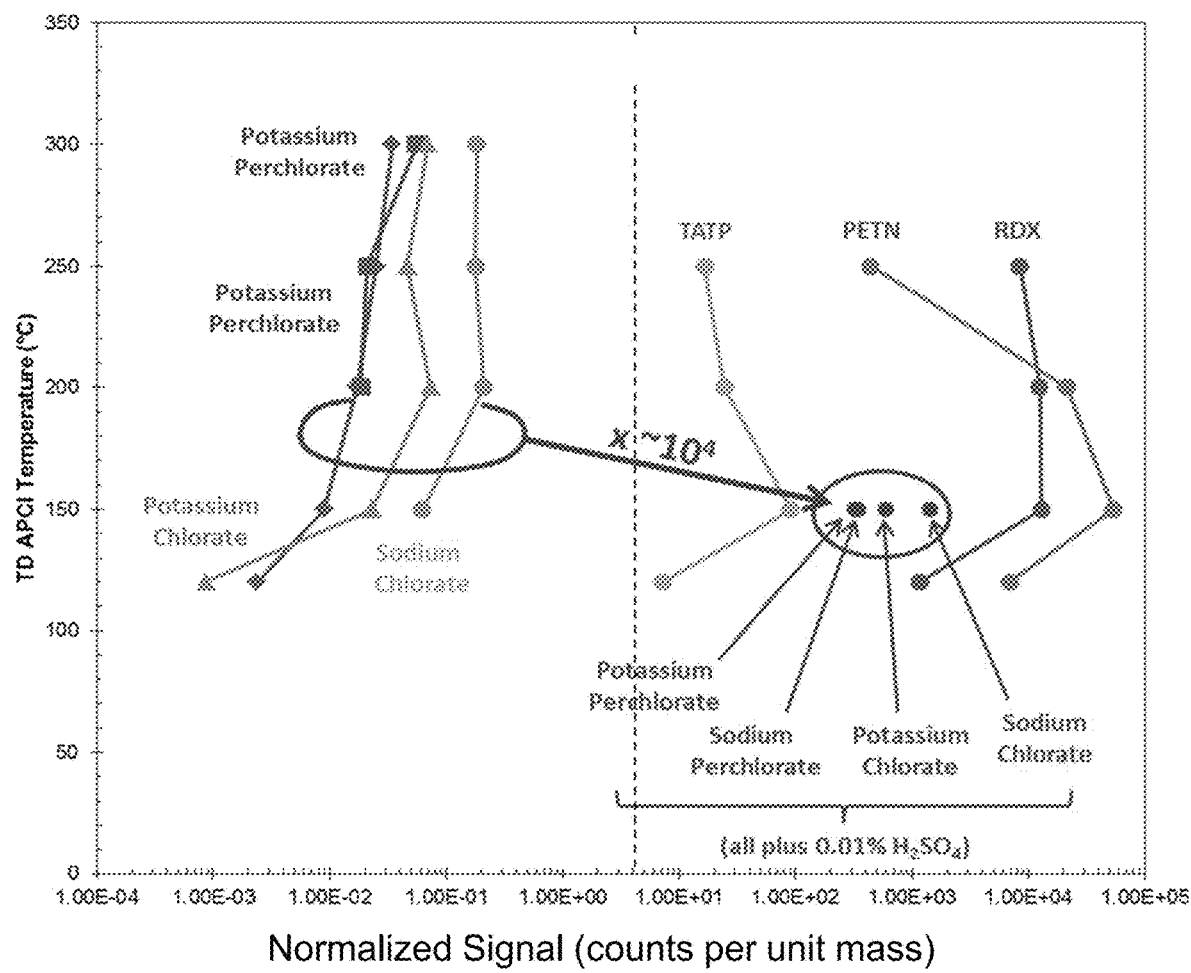
FIG. 10 is a graph of thermal desorption temperature (Y axis) vs. experimentally measured background subtracted normalized mass spectrometer signal (X axis) for detection of chlorate and perchlorate salts (left traces), commonly detected explosive materials (right traces), and oxidizer salts treated with a dilute acidic reagent (red points on the right).

More specifically, FIG. 10 is a graph of thermal desorption temperature (Y axis) vs. experimentally measured background subtracted normalized mass spectrometer signal (X axis) for detection of chlorate and perchlorate salts (left traces), commonly detected explosive materials (right traces), and oxidizer salts treated with a dilute acidic reagent (red points on the right). Increased detection sensitivity is denoted by larger values on the X axis. This figure demonstrates how the presence of an acidic volatilization reagent increases the signal level. The diagonal red arrow in the center of the figure illustrates a $10^4$ factor increase in observed mass spectrometer signal at decreased thermal desorption temperature as a result of treating chlorate and perchlorate salts with dilute sulfuric acid. As shown in FIG. 10, the net result of using the acidic volatilization reagent is increased sensitivity (on the order of a factor of $10^4$ for the dilute sulfuric acid solution used) at a modest thermal desorption temperature of 150° C. It is important to note that this thermal desorption temperature is also near the optimal value for the other more conventionally detected explosives (TATP, PETN, and RDX) included in FIG. 10. This demonstrates that the acidic volatilization reagents can operate in a temperature regime that favors current detection methods and instrumentation.

Example 3

Figure 11:
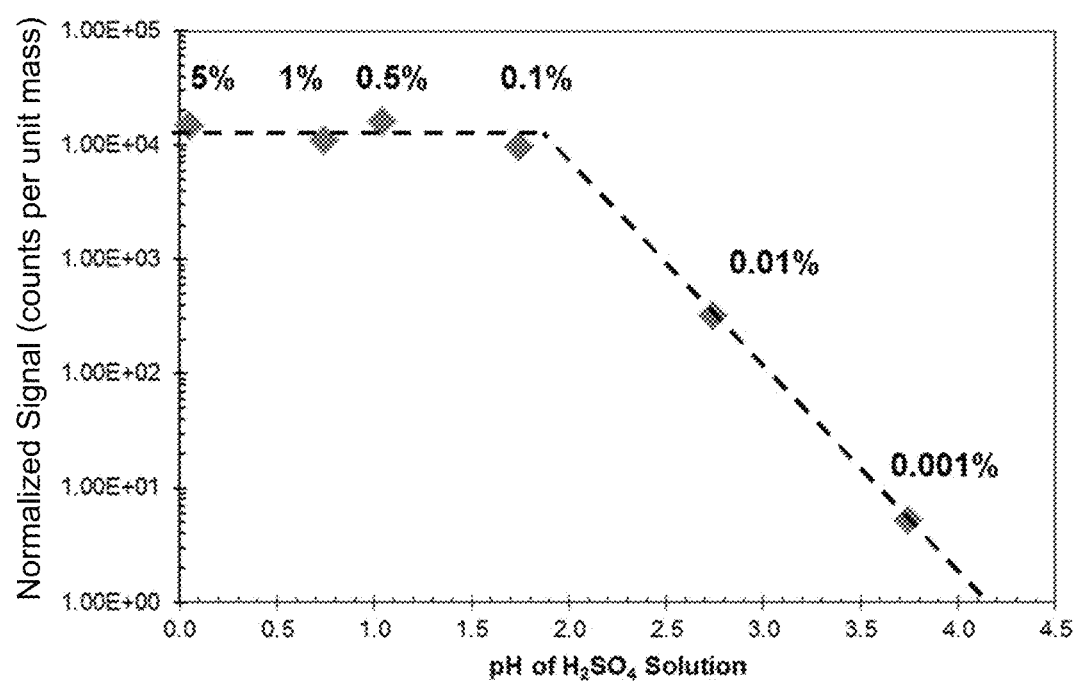
FIG. 11 is a graph of experimentally measured background subtracted normalized mass spectrometer signal (Y axis) vs. pH (X axis) of the acidic volatilization reagent sulfuric acid ($H_2SO_4$) for detection of potassium perchlorate.

In order to determine the minimum acidity (maximum pH) at which the acidic volatilization mechanism was still functional, a series of signal vs. pH measurements were carried out. FIG. 11 shows the results of an experiment conducted in order to determine the maximum acceptable pH for the acidic volatilization reagent sulfuric acid ($H_2SO_4$). FIG. 11 is a graph of experimentally measured background subtracted normalized mass spectrometer signal (Y axis) vs. pH (X axis) of the acidic volatilization reagent sulfuric acid ($H_2SO_4$) for detection of potassium perchlorate. The numbers next to the data points indicate the percent solution (v/v) of sulfuric acid corresponding to each measurement. A 0.01% (pH 2.74) sulfuric acid solution still produces an acceptable amount of signal enhancement for detection of the perchlorate anion. As shown in FIG. 11, the ion signal generated by acid volatilization of potassium perchlorate ($KClO_4$) begins to drop off after a pH of 2 is reached. An acceptable result (in terms of enhancement of the normalized signal compared to bare potassium perchlorate) is still achieved at a pH of 2.74, which is equivalent to a 0.01% sulfuric acid solution.

Example 4

Figure 12:
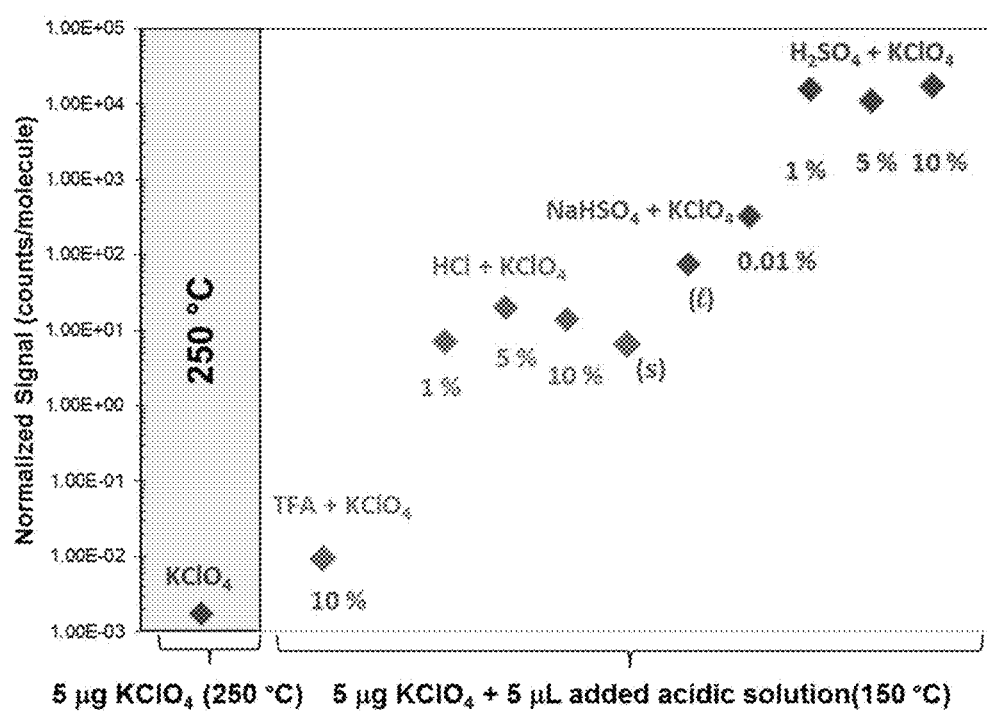
FIG. 12 is a graph showing experimentally measured background subtracted normalized mass spectrometer signal (Y axis) for bare potassium perchlorate at 250° C. and for potassium perchlorate exposed to a variety of different acidic volatilizing reagents at 150° C.

FIG. 12 presents an overview comparing background subtracted normalized mass spectrometer signal for bare potassium perchlorate solid in a TD APCI source and potassium perchlorate treated with a variety of acidic volatilizing reagents. In FIG. 12, experimentally measured background subtracted normalized mass spectrometer signal (Y axis) is shown for bare potassium perchlorate at 250° C. and for potassium perchlorate exposed to a variety of different acidic volatilizing reagents at 150° C. All of the acidic volatilizing agents were presented to the solid potassium perchlorate in liquid form in noted concentrations (v/v) except for the sodium bisulfate data point denoted as solid (s).

Example 5

FIGS. 13A-13D show mass spectra of sodium bisulfate monohydrate enhancing the detection of potassium chlorate. It is clear that the blank background spectrum (FIG. 13A.) and the spectrum of potassium chlorate by itself (FIG. 13B) are markedly similar. Sodium bisulfate monohydrate produces a spectrum of its own (FIG. C). The combination of potassium chlorate and sodium bisulfate monohydrate produces new and unique signals that indicate the presence of chlorate anions ($ClO_3^-$, m/z=83, 85) as well as chlorate breakdown products (chlorite, $ClO_2^-$, at m/z=67, 69 and hypochlorite, $ClO^-$, at m/z=51, 53).

Example 6

It was observed that polymeric acids can be highly effective at enhancing trace detection of inorganic salts with a thermal desorption atmospheric pressure chemical ionization (TD APCI) mass spectrometer. More specifically, both Nafion™ and polystyrene sulfonic acid were observed to enhance detection of chlorates and perchlorates from the milligram/microgram detectable range down to the microgram/nanogram detectable range, an increase in detection on the order of three orders of magnitude.

Figure 14:
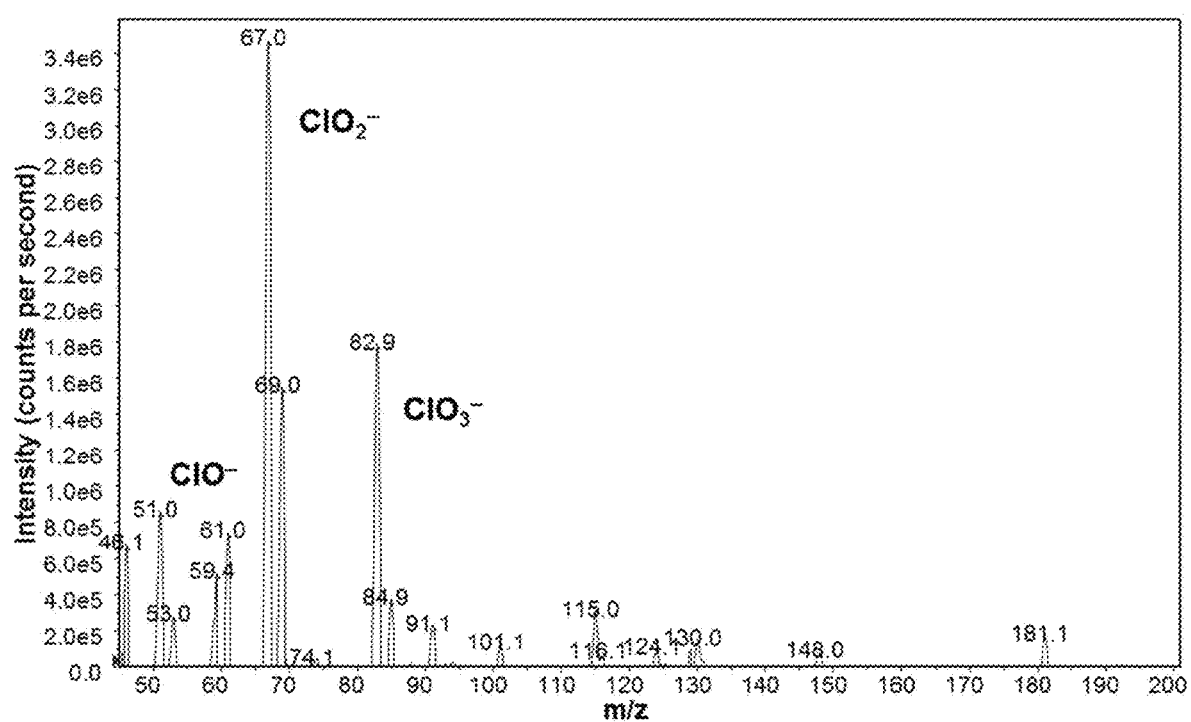
FIG. 14 is a graph of the background subtracted mass spectrum (ion intensity v. mass to charge ratio) for enhanced detection of 5 µg potassium chlorate ($KClO_3$) using 73 µg of Nafion™ as an acidification reagent. The appearance of the ions $ClO_3^-$, $ClO_2^-$ and $ClO^-$ indicates the presence of an inorganic oxidizer salt containing chlorate anions. The thermal desorption temperature was 150° C.
Figure 15:
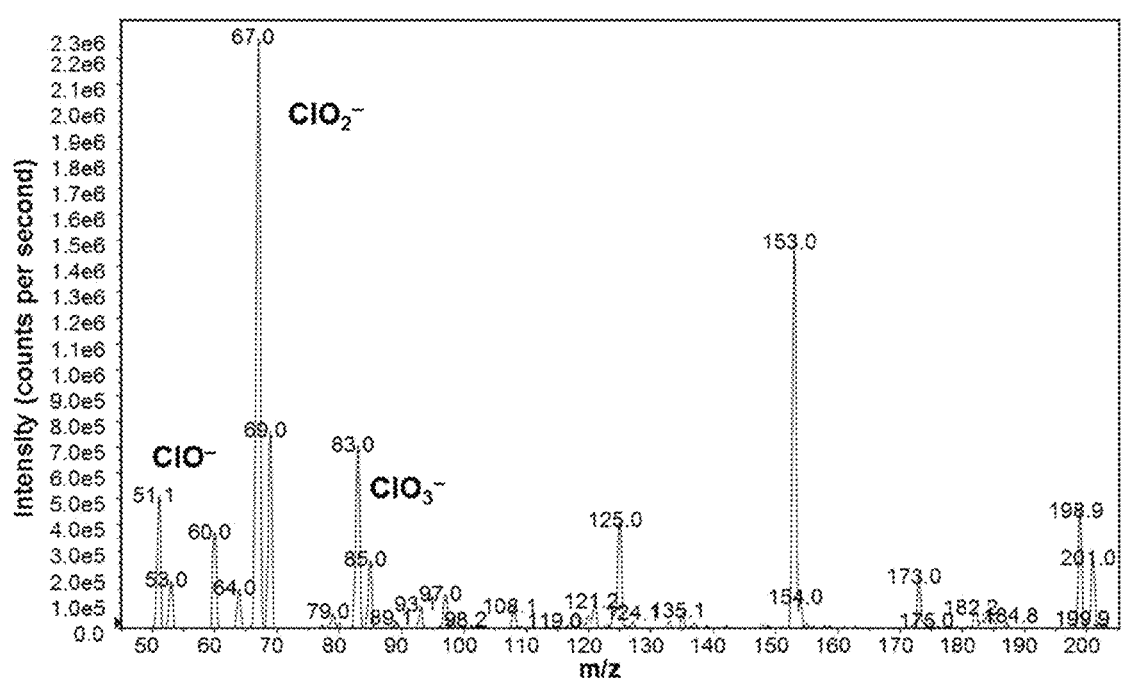
FIG. 15 is a graph of the background subtracted mass spectrum (ion intensity v. mass to charge ratio) for enhanced detection of 0.5 µg potassium chlorate ($KClO_3$) using 900 µg polystyrene sulfonic acid as an acidification reagent. The appearance of the ions $ClO_3^-$, $ClO_2^-$ and $ClO^-$ indicates the presence of an inorganic oxidizer salt containing chlorate anions. The thermal desorption temperature was 150° C.

FIGS. 14 and 15 present representative mass spectra showing detection of potassium chlorate ($KClO_3$) with both Nafion™ and polystyrene sulfonic acid, respectively. It is clear that these polymeric acids are strong enough to enable the acidification/volatilization, and their hygroscopic property ensures that they carry enough absorbed water to enable the reaction to proceed in an efficient manner. The relative lack of clutter in these mass spectra indicates that these polymeric acids are enabling the acidification/volatilization mechanism without introducing unwanted by-products to the gas phase ion population.

One skilled in the art will appreciate further features and advantages of the invention based on the above-described embodiments. Accordingly, the invention is not to be limited by what has been particularly shown and described, except as indicated by the appended claims. All patents, publications and references cited herein (including the following listed references) are expressly incorporated herein by reference in their entirety.

The invention claimed is:

1. A swipe for detection of an analyte, comprising:
a substrate configured to collect a sample for analysis, and
a proton-containing acidic reagent associated with the substrate and configured to react with an analyte, if present in the sample, to transfer a proton to the analyte so as to generate a higher vapor pressure analog of the analyte,
wherein the acidic reagent comprises a polymeric acid, and
a thermally labile hydrate that can provide an additional source of water upon heating, thereby facilitating reaction of the proton-containing acidic reagent with the analyte.

2. The swipe of claim 1, wherein the thermally labile hydrate comprises sodium thiosulfate pentahydrate.

3. The swipe of claim 1, wherein the analyte is an ionic component of an explosive material.

4. The swipe of claim 3, wherein said ionic component is selected from the group consisting of salts of chlorate, perchlorate, permanganate, dichromate, and osmium tetraoxide.

5. The swipe of claim 1, wherein the acidic reagent has a pKa of less than 2.5.

6. The swipe of claim 5, wherein said acidic reagent comprises a polymeric organic acid.

7. The swipe of claim 1, wherein the acidic reagent is a polymeric organic acid.

8. The swipe of claim 1, wherein the acidic reagent comprises a hydrated acidification reagent.

9. The swipe of claim 8, wherein the hydrated acidification reagent comprises a hydrated solid state acid.

10. The swipe of claim 9, wherein said hydrated solid state acid comprises a hydrated sulfonate—or sulfate-containing acid.

11. The swipe of claim 1, wherein said acidic reagent exists in the solid or liquid phase.

\* \* \* \* \*